(12) United States Patent
Khanna

(10) Patent No.: US 10,434,008 B2
(45) Date of Patent: Oct. 8, 2019

(54) CENTRAL NERVOUS SYSTEM TREATMENT DEVICE AND METHODOLOGY

(76) Inventor: Rohit Khanna, Daytona Beach, FL (US)

( * ) Notice: Subject to any disclaimer, the term of this patent is extended or adjusted under 35 U.S.C. 154(b) by 547 days.

(21) Appl. No.: 13/107,916

(22) Filed: May 15, 2011

(65) Prior Publication Data

US 2012/0221082 A1 Aug. 30, 2012

Related U.S. Application Data

(63) Continuation-in-part of application No. 11/418,849, filed on May 5, 2006, now Pat. No. 8,123,789.

(51) Int. Cl.
*A61F 7/12* (2006.01)
*A61F 7/00* (2006.01)

(52) U.S. Cl.
CPC ........ *A61F 7/12* (2013.01); *A61F 2007/0056* (2013.01); *A61F 2007/126* (2013.01)

(58) Field of Classification Search
USPC .................................................. 607/105, 113
See application file for complete search history.

(56) References Cited

U.S. PATENT DOCUMENTS

| | | | |
|---|---|---|---|
| 4,904,237 A | 2/1990 | Janese | |
| 6,338,727 B1 | 1/2002 | Noda et al. | |
| 6,379,331 B2 | 4/2002 | Barbut et al. | |
| 6,506,189 B1 | 1/2003 | Rittman et al. | |
| 6,527,798 B2 | 3/2003 | Ginsburg et al. | |
| 6,660,026 B2 | 12/2003 | Larnard et al. | |
| 6,682,508 B1 | 1/2004 | Maythaler et al. | |
| 6,699,269 B2 | 3/2004 | Khanna | |
| 6,849,072 B2 | 2/2005 | Lee et al. | |
| 6,899,726 B2 | 5/2005 | Larnard et al. | |
| 7,004,961 B2 | 2/2006 | Wong et al. | |
| 7,144,418 B1 * | 12/2006 | Lennox | A61F 7/123 607/105 |
| 7,318,834 B2 | 1/2008 | Njemanze | |
| 8,123,789 B2 | 2/2012 | Khanna | |
| 2002/0198579 A1 | 12/2002 | Khanna | |
| 2003/0135252 A1 * | 7/2003 | MacHold | A61M 25/10 607/106 |
| 2004/0133256 A1 * | 7/2004 | Callister | 607/105 |
| 2004/0138728 A1 * | 7/2004 | Wong et al. | 607/105 |
| 2007/0005121 A1 | 1/2007 | Khanna | |
| 2011/0029050 A1 * | 2/2011 | Elefteriades | A61F 7/12 607/105 |

\* cited by examiner

*Primary Examiner* — Joseph A Stoklosa
*Assistant Examiner* — Adam J Avigan
(74) *Attorney, Agent, or Firm* — Wenderoth, Lind & Ponack, L.L.P.

(57) ABSTRACT

The invention relates to a method of central nervous system pathology treatment through selective hypothermia. Brain and spinal cord cooling is achieved through a closed loop catheter system inserted directly into the cerebrospinal fluid space. The catheter comprises of a portion that dilates in a pulsatile or peristaltic fashion and facilitates circulation of the cooled cerebrospinal fluid.

20 Claims, 19 Drawing Sheets

CENTRAL NERVOUS SYSTEM TREATMENT DEVICE AND METHODOLOGY

BACKGROUND OF THE INVENTION

The current invention relates to regulation of the temperature in the brain and spinal cord. The invention describes a method and apparatus for altering the temperature of the brain and/or the cerebrospinal fluid in the ventricles of the brain and surrounding the brain and spinal cord.

Hypothermia has been shown to provide cerebral and spinal cord injury protection from either trauma, ischemia, or hypoxia. Ischemia may occur from cardiac arrest, cardiac failure, stroke, head or spinal cord injury, aneurysm surgery, cardiac surgery, and aortic or carotid surgery. Hypothermia is also effective in reducing increased intracranial pressure from cerebral swelling. The mechanisms involved in hypothermic cerebral protection are several-fold and include 1) reduction in cerebral glucose and oxygen metabolism and decreasing lactate content following injury, 2) preventing disruption of the blood brain barrier and consequently reducing cerebral edema, 3) reduction of endogenously toxic neurotransmitters like glutamate, glycine, aspartate, acetylcholine, and norepinephrine into the brain after injury, 4) inhibit excessive calcium entry and intracellular calcium overload into neurons, 5) protecting membrane structural proteins like microtubule-associated protein-2, and 6) preventing diffuse axonal injury following brain trauma.

In general, the human brain and spinal cord are maintained at a constant temperature of approximately 37 to 38 degrees celsius. Hypothermia is considered mild when the body temperature is 33 to 35 degrees celsius, moderate between the temperatures of 28 to 32 degrees, and severe in the temperature range of 24 to 28 degrees celsius. Most studies in humans have involved mild to moderate systemic hypothermia mainly because of the significant side effects that occur from induced systemic hypothermia. These include infection, cardiac arrhythmias, coagulopathy, renal failure, as well as rewarming shock. In order to avoid these complications the degree and duration of hypothermia has been shortened thereby limiting its effectiveness.

Generally, cooling of the brain has been accomplished through whole body cooling with use of a cooling blanket, immersing the patient in ice, or cooling the blood through a cardiopulmonary bypass machine. A few methods have been described regarding selective brain and spinal cord hypothermia. These involve cooling the arterial vessel or blood supply to the brain or external cooling helmets, each with its own significant limitations.

Several catheters have been developed to induce systemic hypothermia by inserting them into the bloodstream. More recently catheters have been developed that can be inserted into the arterial vessels to the brain to induce selective brain hypothermia. These catheters are limited in their size and functionality by the small vessel lumen as well the inability to cool all the four major arterial vessels supplying blood to the brain and are unable to cool the spinal cord via this methodology. They also carry the risk of ischemic and thromboembolic stroke by either impairing the blood flow to the brain or dislodging clots that can develop in intra-arterial catheters.

External cooling helmets have limited effectiveness since the blood to the cooled scalp does not circulate into the brain and returns systemically which along with the thick skull dilutes the hypothermic effect to the brain.

Selective brain and spinal cord cooling with insertion of closed loop system catheters into the ventricular, subdural or epidural space was first described in U.S. Pat. No. 6,699,269 to Khanna. It also describes a catheter that expands with circulation of a coolant without direct contact of the coolant with the central nervous system. This avoids the side effects and complications seen from other methods of cooling. It also circumvents infection and fluid overload with exacerbation of brain swelling that can be potentially encountered with cooling systems involving circulating the cerebrospinal fluid. This patent also relates a methodology for cerebrospinal fluid drainage to relieve an increase in ICP. U.S. application Ser. No. 11/418,849 by the applicant relates a method and apparatus for selective central nervous system cooling with a balloon catheter. Although the balloon is used to increase the surface area of cerebrospinal fluid contact to facilitate heat exchange, all of the prior art relates dilation of the balloon to a preset volume. Balloon dilation inside the central nervous system has a significant potential for raising the intracranial pressure especially when there is pathology and/or swelling in the brain and spinal cord. Dilating the balloon to a preset volume may not be the best methodology since different patients will tolerate different levels of central nervous system volume increase. Even a few milliliters of volume increase inside the head or spine with a swollen brain and spinal cord can risk severe further injury. Another limitation of the prior technique is cooling of the cerebrospinal fluid in a stagnant cerebrospinal fluid which limits the extent of selective central nervous system cooling. There remains a need for faster and more uniform methodology for selective central nervous hypothermia induction and central nervous system pathology treatment.

SUMMARY OF THE INVENTION

The invention provides a method and apparatus for treatment of central nervous system pathology. This is achieved by performing selective hypothermia to the brain and/or the spinal cord for injury protection without the need for systemic cooling as well as drainage any excess cerebrospinal fluid or hemorrhage through the device.

For selective brain cooling, in one embodiment of the present invention, a flexible heat exchange catheter is inserted into the cerebrospinal fluid space. The catheter has an inflow and outflow lumen for circulation of a coolant by an external regulator. The portion of the catheter in contact with the cerebrospinal fluid can expand into a balloon in a peristaltic format. The peristaltic expansion and contraction creates pulsations in the cerebrospinal fluid and circulates the cooled cerebrospinal fluid, thereby uniformly cooling the brain and spinal. Cerebrospinal fluid is produced by the choroid plexus inside the brain lateral ventricles. The two lateral ventricles communicate with each other through the third ventricle which also opens into the fourth ventricle. The lateral ventricles also communicate with the cerebrospinal fluid in the basal cisterns surrounding the brain stem through the choroidal fissure. The fourth ventricle communicates with the subarachnoid space through the foramen of Magendie and Luschka. The subarachnoid space extends from around the brain, brainstem, and spinal cord. Essentially all of the central nervous system structures and in particular the brain and spinal cord either are surrounded by or contain cerebrospinal fluid. A methodology that not only cools the cerebrospinal fluid but also facilitates circulation of the cooled cerebrospinal fluid provides for a faster and more uniform selective central nervous system hypothermia induction.

In another embodiment, the catheter has three lumens with two lumens used for circulation of the coolant that communicate at the distal end of the catheter. The third lumen has holes at the distal end that allows for drainage of cerebrospinal fluid as well as intracranial pressure monitoring similar to a ventriculostomy. An external regulator controls the extent of balloon dilation and coolant rate circulation by maintaining the central nervous system pressure within a desirable range. In another embodiment of the catheter, a balloon located at the distal end of the catheter expands when the coolant fluid is circulated. The expansion also opens the third lumen distal holes further to maintain patency.

In other embodiments, the balloon expansion is controlled and can also conform to the space of the central nervous system location that it is placed in as long as the central nervous system pressure remains within a desirable range preferably within normal limits of less than 15 mm Hg.

The catheters are designed to allow an inert coolant to circulate in the lumens without direct exposure to the brain or spinal cord and thereby altering the brain or spinal cord temperature. This allows for selective cooling of the brain and spinal cord for treatment of injury from trauma, ischemia, hypoxia and/or cerebral swelling.

DETAILED DESCRIPTION OF THE PREFERRED EMBODIMENTS

Figure 1:
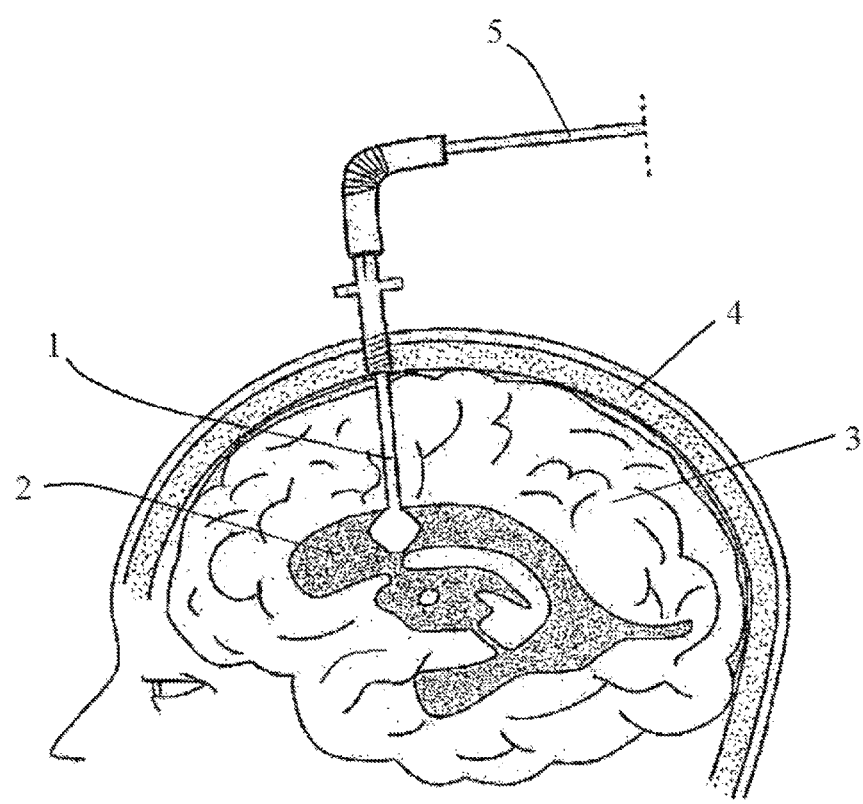
FIG. 1 is a schematic view of one embodiment the device in the brain lateral ventricle.
Figure 2A:
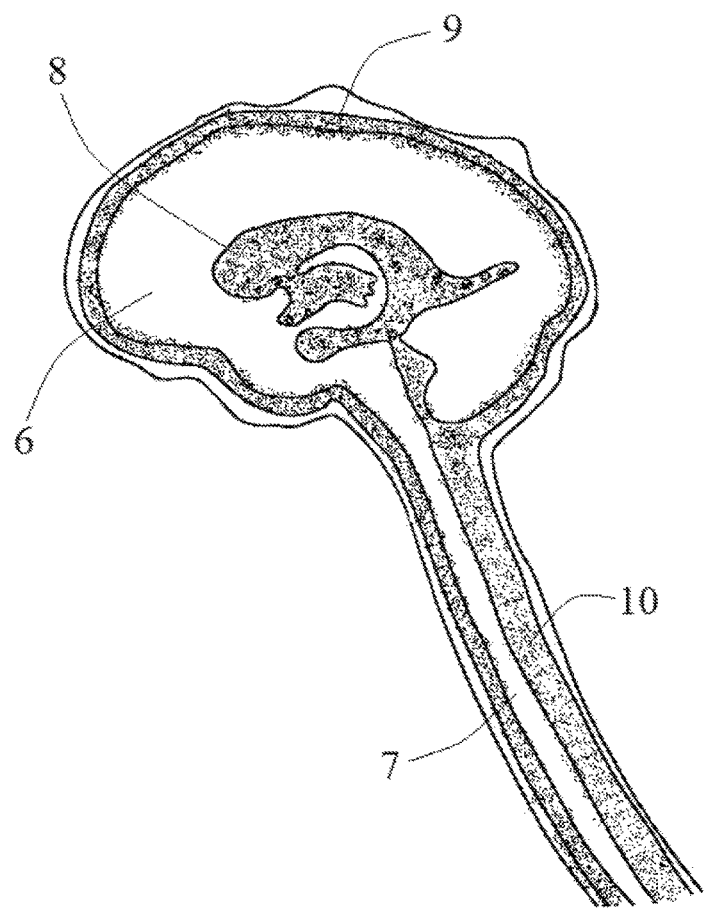
FIG. 2a is a schematic view of the central nervous system and cerebrospinal fluid.
Figure 2B:
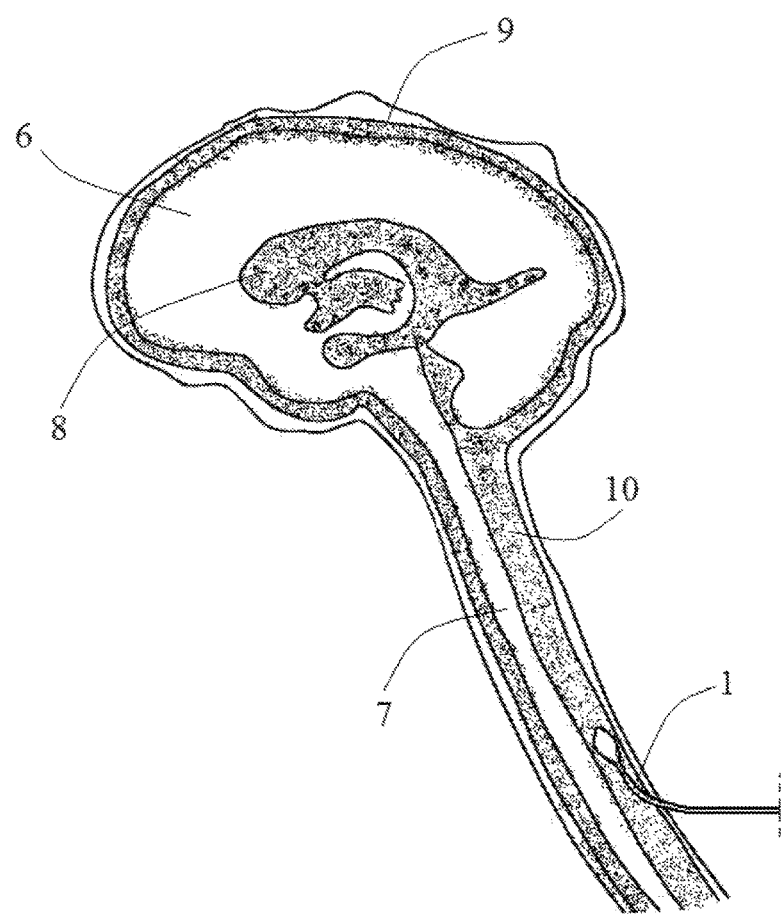
FIG. 2b is a schematic view of the device in the spinal subarachnoid cerebrospinal fluid space.

In one method of central nervous system pathology treatment, the device as shown in FIG. 1, is placed into the ventricle of the brain or the subarachnoid space of the spine. This allows for cooling of the cerebrospinal fluid and hence the brain and/or spinal cord selectively. The effects of the cooling provide for treatment of swelling, traumatic, hypoxic, and ischemic injuries. These devices can be placed in the lateral ventricles using the standard landmarks or can be precisely placed with stereotactic guidance or use of an endoscope or ultrasound. The device 1 is placed into the cerebrospinal fluid in the ventricle 2 of the brain 3. Typically a hole is drilled into the skull 4 to access the brain and the ventricles through a standard ventriculostomy approach. The device 1 distal end comprises a balloon placed in the cerebrospinal fluid that allows a greater surface area for heat exchange. The proximal end 5 of the device 1 is connected to a regulator that controls the extent of balloon dilation and circulation of the coolant through the device 1 closed loop cooling system. The regulator also monitors ICP and temperature through sensors positioned near the balloon end of the device 1. As shown in FIGS. 2a & 2b, the brain 6 contains cerebrospinal fluid inside the ventricles 8 and is also surrounded by cerebrospinal fluid 9 which is in communication with the cerebrospinal fluid 10 around the spinal cord. Cooling of the cerebrospinal provides for selective hypothermia of the brain and spinal cord. Facilitating circulation of the cooled cerebrospinal fluid provides for a faster brain and spinal cord cooling. The cerebrospinal fluid circulation can be facilitated by a device 1 placed in the cerebrospinal fluid 10 with a balloon that dilates and contracts in an alternating sequence or a peristaltic format as described in the current invention. This sequential dilation and contraction circulates the cerebrospinal fluid inside and outside the brain and spinal cord. It is also very prudent that the extent of the device balloon dilation placed inside the central nervous system be controlled so that the ICP is not increased in this process and also avoid compressive forces on the brain or spinal cord. A balloon that conforms to the shape of the space it has been placed inside the central nervous system allows for the best possible likelihood of not increasing the ICP with balloon dilation. The balloon shape can be round, oval, cylindrical or conform to the shape of the portion of the lateral ventricle it is placed in to avoid compression against the ventricle wall. The preferred spinal cerebrospinal fluid space location of the device is in the lumbar location but can also include cervical or thoracic spine. The device can be placed post-operatively after either a laminectomy, discectomy, or corpectomy. The device can also be placed through a percutaneous technique similar to placement of a spinal drain or lumbar puncture. X-ray or fluoroscopy can also be used to locate the correct spinal placement of the device.

Figure 3A:
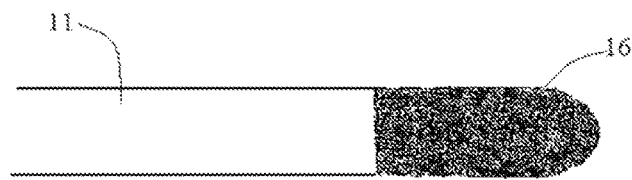
FIG. 3a is a side view of the device.
Figure 3B:
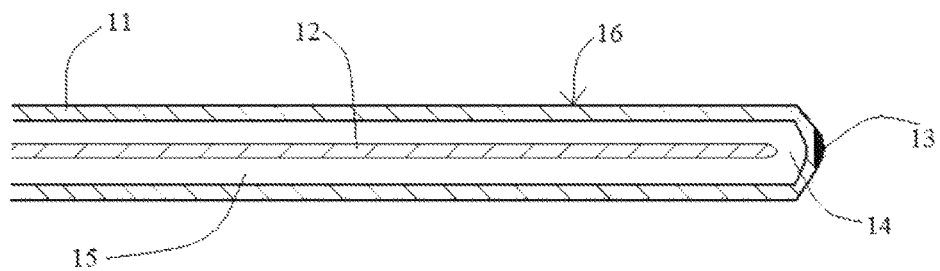
FIG. 3b is a longitudinal cross-sectional view of the device.
Figure 4:
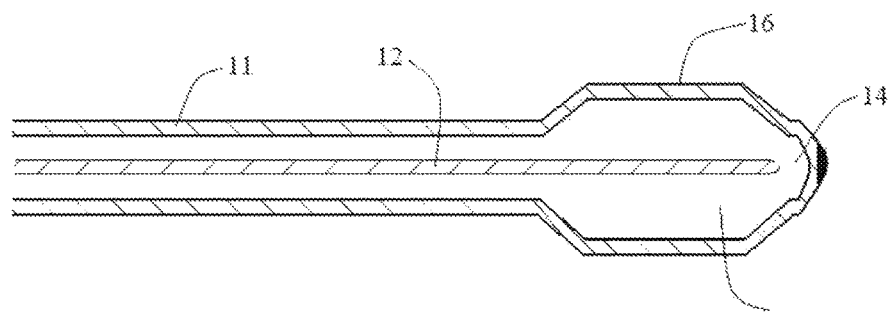
FIG. 4 is a longitudinal cross-sectional view of the device with partially dilated balloon.
Figure 5:
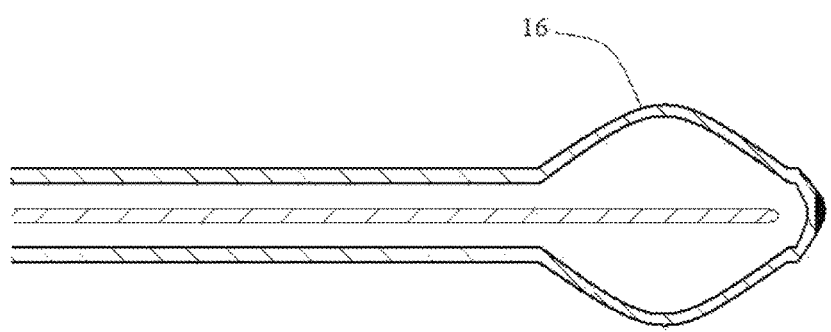
FIG. 5 is a longitudinal cross-sectional view of the device with fully dilated balloon.
Figure 6:
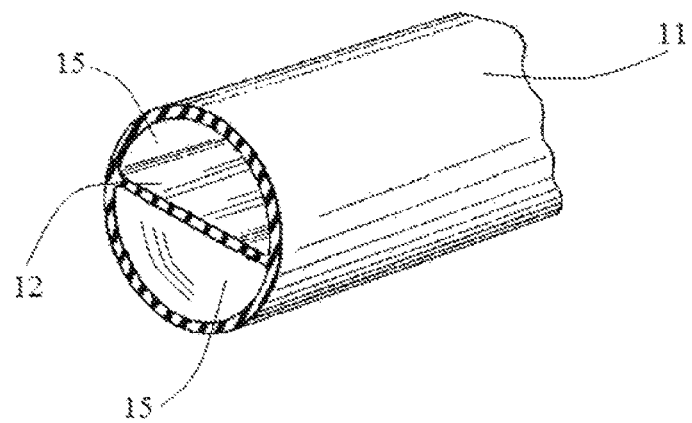
FIG. 6 is a partial sectional view of the device.
Figure 7:
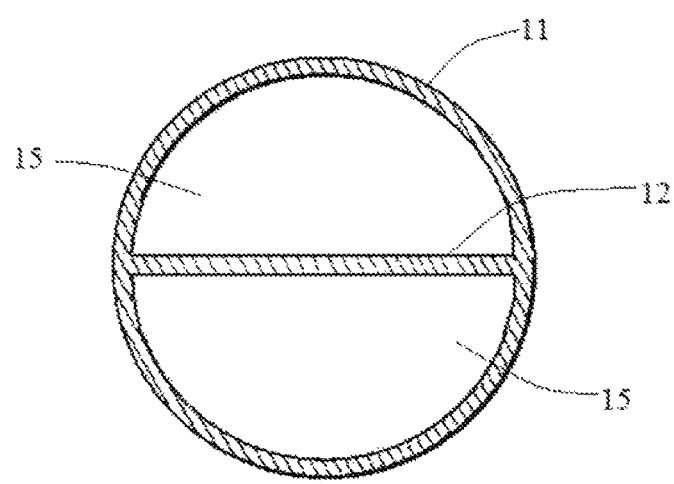
FIG. 7 is a cross-sectional view of the device.

In one embodiment as shown in FIGS. 3-7, the device is in the contracted position of the balloon 16 as shown in FIGS. 3a & 3b and dilated balloon positions as shown in FIGS. 4 & 5. The device comprises an outside wall 11 and an inside wall 12. The inside wall divides the lumen of the device into two parts 15 that communicate at the distal end 14. The lumens circulate a coolant through a regulator/coolant placed external to the body. The device distal end is placed inside the desired central nervous system location. The distal end also comprises of one or more sensors 13 (pressure, temperature, etc). FIG. 4 shows the distal end 16 of the device in a partially dilated balloon position and FIG. 5 shows the distal balloon 16 completely dilated. The pulsating dilation and contraction of the balloon 16 circulates the cerebrospinal fluid outside the balloon and the circulating coolant in the lumens cools the cerebrospinal fluid. The increased surface area provided by the balloon expansion allows for a greater degree of heat exchange.

Figure 8A:
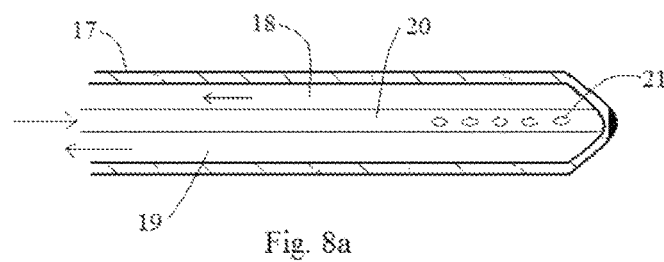
FIG. 8a is a longitudinal cross-sectional view of another embodiment of the device.
Figure 8B:
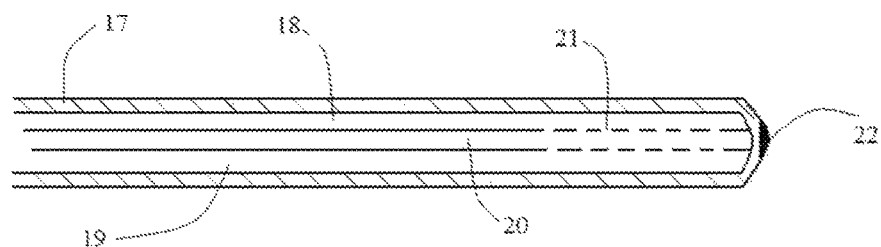
FIG. 8b is a longitudinal cross-sectional view of the device with the balloon in a contracted position.
Figure 9A:
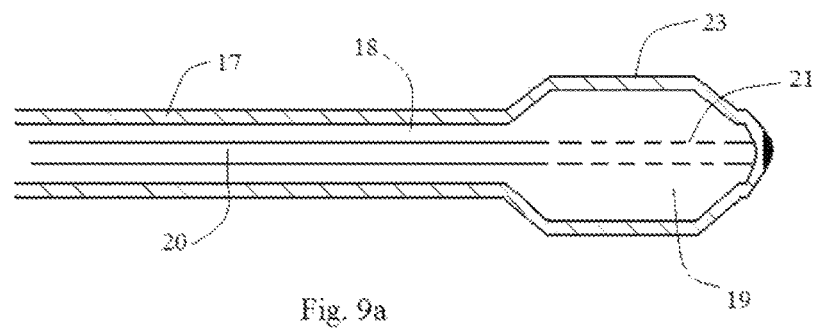
FIG. 9a is a longitudinal cross-sectional view of the device with the balloon in a partially dilated position.
Figure 9B:
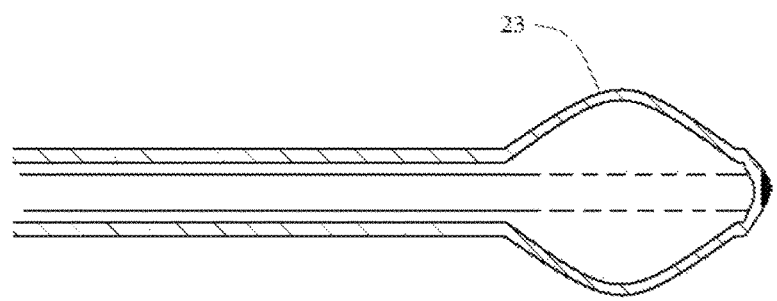
FIG. 9b is a longitudinal cross-sectional view of the device with the balloon in a fully dilated position.

In another embodiment as shown in FIGS. 8 & 9, the device comprises a catheter with a wall 17 and a central lumen 20 surrounded by a lumen 18 and 19. The lumen 20 communicates with the lumen 18 and 19 through holes 21 at the distal end of the catheter and circulates a coolant with the arrows in FIG. 8a depicting the direction of the coolant flow. The catheter also contains sensors 22 at the distal portion. The contracted shape of the balloon is shown in FIGS. 8a & 8b and the expanded shape of the balloon 23 is shown in FIGS. 9a & 9b. The balloon 23 is partially dilated in FIG. 9a and completely dilated in FIG. 9b. The balloon 23 expands and contracts in a pulsating format with circulation of the coolant by an external coolant pump regulator. This pulsating expansion and contraction of the balloon creates a wave in the cerebrospinal fluid where the balloon tip is placed and facilitates circulation of the cooled cerebrospinal fluid throughout the central nervous system.

Figure 10:
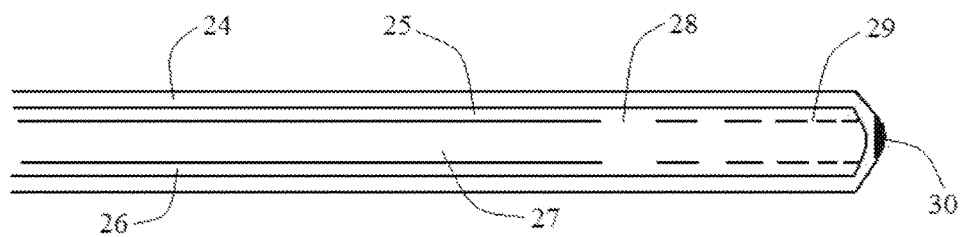
FIG. 10 is a longitudinal cross-sectional view of another embodiment the device with the balloon in a contracted position.
Figure 11:
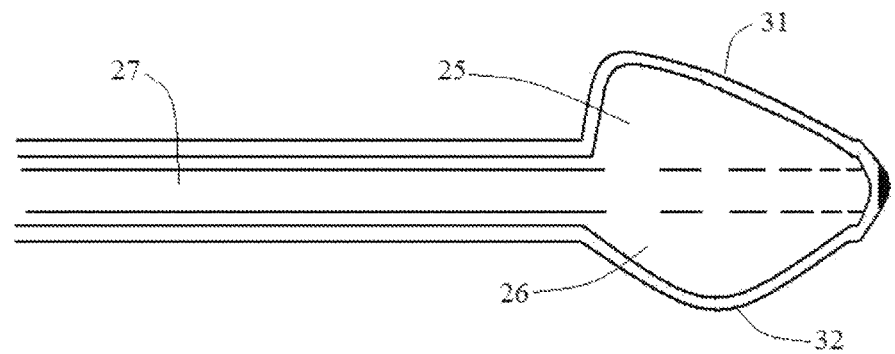
FIG. 11 is a longitudinal cross-sectional view of the device with the balloon in a partially dilated position.
Figure 12:
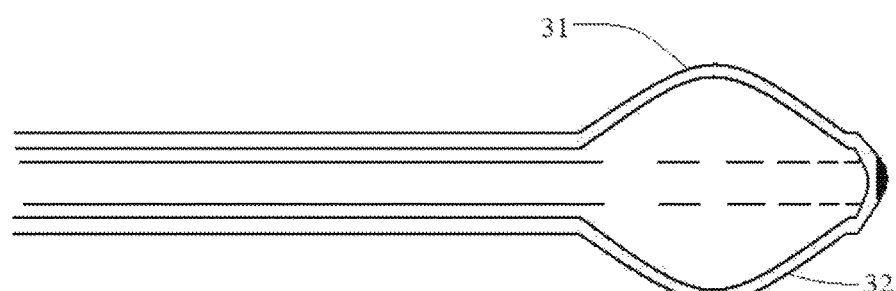
FIG. 12 is a longitudinal cross-sectional view of the device with the balloon in a fully dilated position.

In another embodiment of the device as shown in FIGS. 10-12, the catheter comprises a wall 24 with a central lumen 27 that communicates with the lumen 25 and 26 surrounding the central lumen 27 through holes 28 and 29. The holes in the distal portion of the central lumen 27 are larger in diameter proximally 28 and decrease in diameter sequentially distally 29. The coolant is circulated through the lumen 27 and exits into lumen 25 and 26 through the holes 28 and 29 in a closed loop system. The distal catheter wall 31 can dilate if the pressure in the lumen is increased by an external coolant regulator. The larger holes 28 proximally and smaller holes 29 distally in the central lumen 27 allow larger coolant flow more proximally into lumen 25 and 26 thereby dilating the balloon in a peristaltic format as shown in FIGS. 11 & 12. In FIG. 11, the top portion of the balloon 31 is dilated more proximally and the dilation wave progresses more distally as seen with the bottom portion of the balloon 32. This peristaltic format of balloon dilation with circulation of the coolant moves the cooled cerebrospinal surrounding the balloon and facilitates central nervous system cooling.

Figure 13:
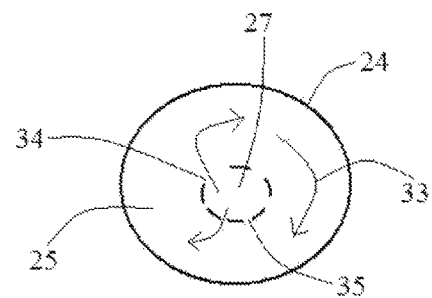
FIG. 13 is a cross-sectional view of another embodiment the device depicting direction of coolant flow.

In another embodiment of the catheter as shown in FIG. 13, the central lumen 27 is surrounded by lumen 25 with an outer wall 24. The central lumen 27 communicates with surrounding lumen 25 at the distal catheter end through holes 34 and 35 which enlarge circumferentially. This enables the wall 24 to dilate into a balloon in a peristaltic and spiraling format with circulation of the coolant 33 (arrows depicting flow direction). This balloon dilation format further facilitates circulation of the cooled cerebrospinal fluid surrounding the balloon.

Figure 14:
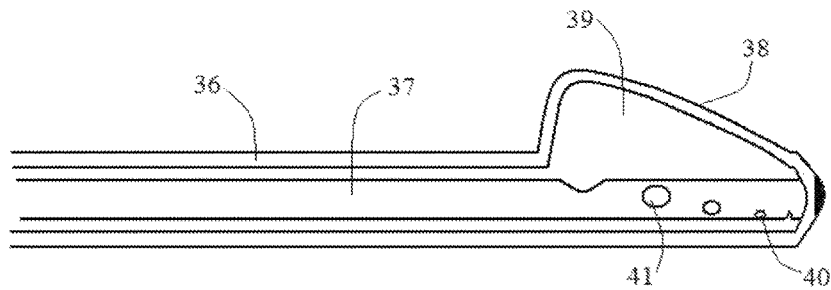
FIG. 14 is a longitudinal cross-sectional view of another embodiment the device with the balloon in a partially dilated position.
Figure 15:
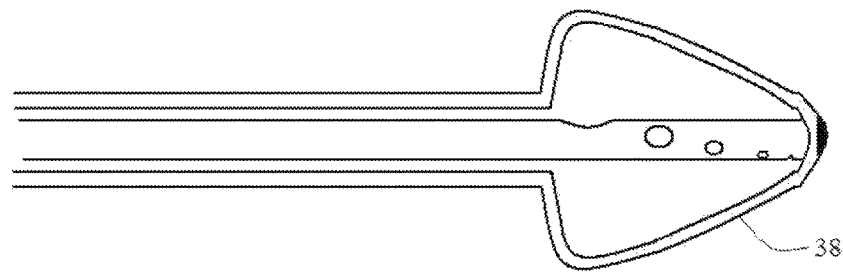
FIG. 15 is a longitudinal cross-sectional view of the device with the balloon in a partially dilated position.
Figure 16:
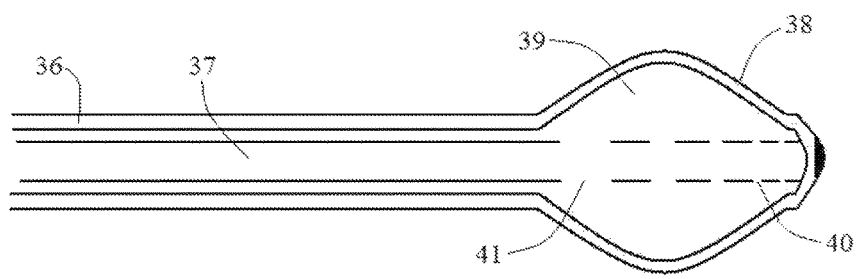
FIG. 16 is a longitudinal cross-sectional view of the device with the balloon in a fully dilated position.

In another embodiment of the catheter as shown in FIGS. 14-19, the central lumen 37 is surrounded by a lumen 39 and catheter wall 36. The central lumen is attached to the outer wall by a membrane 47. The central lumen 37 comprises holes 40 and 41 at the distal end. The holes are larger proximally 41 and taper to a smaller size 40 distally. The holes 41 and 40 also taper from a larger to smaller size in a spiraling format. With circulation of the coolant the outer catheter wall expands into a balloon from proximally to distally in a spiraling and peristaltic format. FIG. 14 shows the balloon 38 dilation in the initial phase, FIG. 15 shows circumferential balloon dilation 38, and FIG. 16 shows the peristaltic balloon dilation 38 moving from proximal to the distal end.

Figure 17:
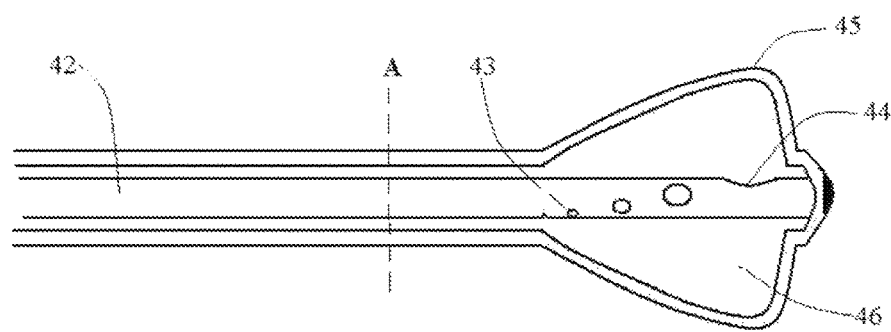
FIG. 17 is a longitudinal cross-sectional view of another embodiment the device with the balloon in a partially dilated position.
Figure 18:
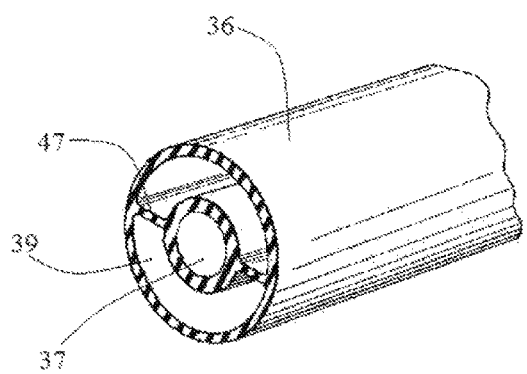
FIG. 18 is a partial sectional view of the device.
Figure 19:
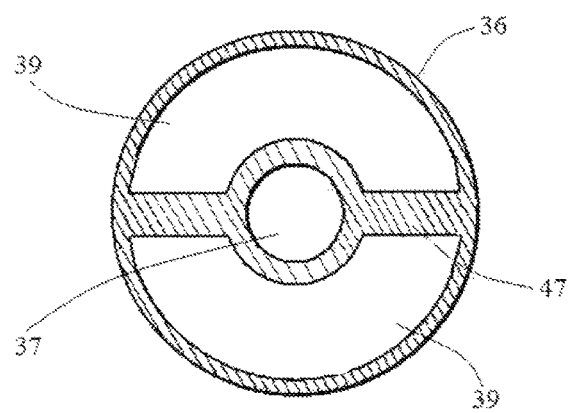
FIG. 19 is a cross-sectional view of the device.
Figure 20:
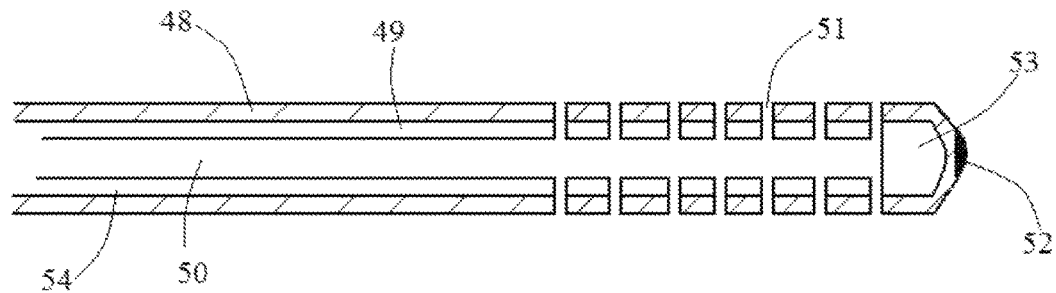
FIG. 20 is a longitudinal cross-sectional view of another embodiment the device with the balloon in a contracted position.

FIG. 17 illustrates another embodiment of the spiral peristaltic balloon dilation catheter. The central lumen 42 comprises holes 43 and 44 at the distal end surrounded by a lumen 46 and balloon wall 45. The lumen 42 holes enlarge from a smaller 43 to larger 44 sizes from proximal to distal end in a spiraling format. Circulation of the coolant dilates the balloon 45 in a spiral peristaltic manner from distally to proximally.

Figure 21:
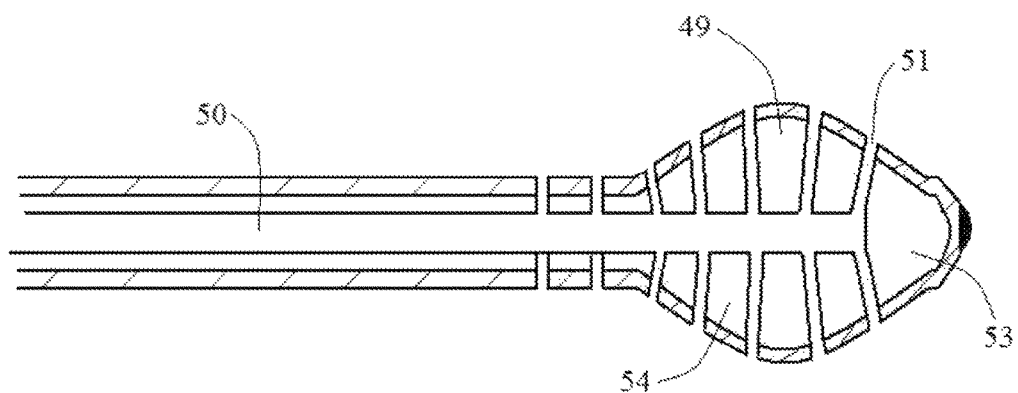
FIG. 21 is a longitudinal cross-sectional view of the device with the balloon in a dilated position.
Figure 22:
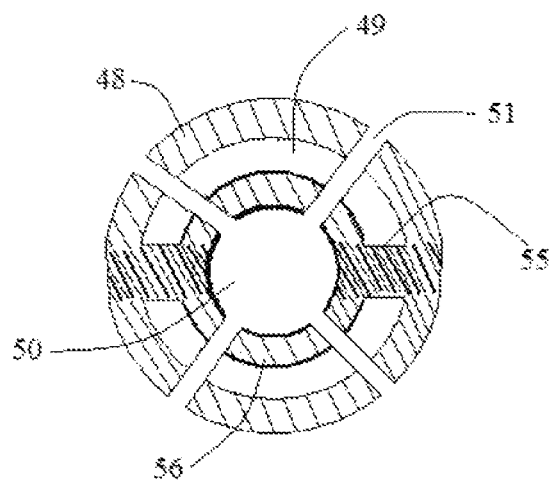
FIG. 22 is a cross-sectional view of the device with the balloon in a contracted position.
Figure 23:
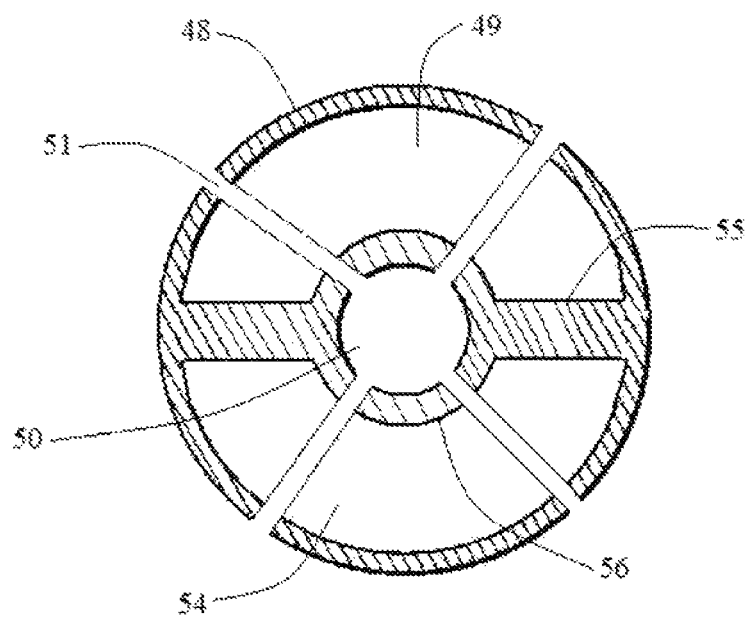
FIG. 23 is a cross-sectional view of the device with the balloon in a dilated position.

In another embodiment of the device as shown in FIGS. 20-23, the catheter also comprises a drainage lumen with ports at the distal end. The lumen 49 and 54 is contained between the catheter outer wall 48 and the inner wall 56. The inner lumen 50 is used for drainage of cerebrospinal fluid and/or hemorrhage through ports 51. This lumen can also be used to monitor intracranial pressure similar to a ventriculostomy drain. The lumen wall 56 is attached to the lumen wall 48 with membrane 55. A coolant is circulated in the lumens 49 and 54 which communicate at the distal end 53 with a closed loop system. A temperature and/or pressure sensor 52 is positioned at the tip or any other location on the catheter to monitor central nervous system temperature and/or pressure. The distal portion of the catheter is capable of dilating into a balloon with circulation of the coolant under controlled pressure with dilation of the lumen 49 and 54 spaces as shown in FIGS. 21 and 23.

Figure 24:
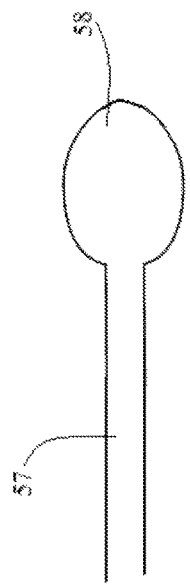
FIG. 24 is a side view of another embodiment of the device.
Figure 25:
FIG. 25 is a side view of another embodiment of the device.
Figure 26:
FIG. 26 is a side view of another embodiment of the device.

The balloons located at the distal catheter ends can conform to the shape of the central nervous system space that they are placed in. The balloon walls are compliant and conform to the shape most amenable to not increasing the intracranial pressure. FIGS. 24-26 illustrate the various embodiments with different balloon shapes including but not limited to the shapes illustrated. FIG. 24 shows an inflow and outflow coolant circulation lumen 57 with a round balloon 58, FIG. 25 shows an inflow and outflow lumen 59 with an oval balloon 60, and FIG. 26 illustrates an inflow and outflow lumen 61 with a cylindrical balloon 62. Other balloon shapes can comprise of a shape of the lateral ventricle, post-surgical brain cavity, cisterna magna, subdural, epidural or subarachnoid space in the head or spine. The balloons can dilate parallel to the longitudinal catheter axis or at any other angle from 0 to 360 degrees.

Figure 27:
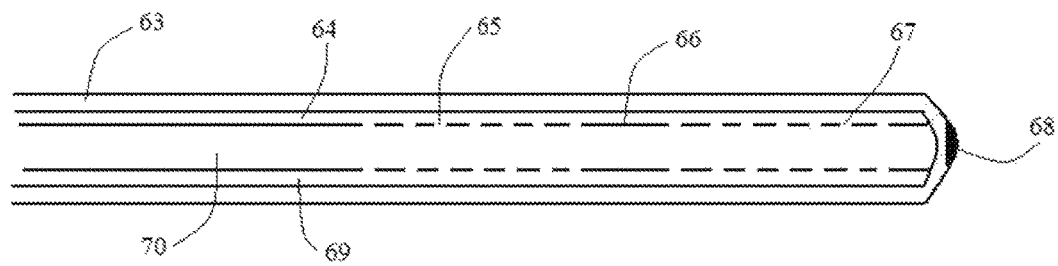
FIG. 27 is a longitudinal cross-sectional view of another embodiment the device with the balloon in a contracted position.
Figure 28:
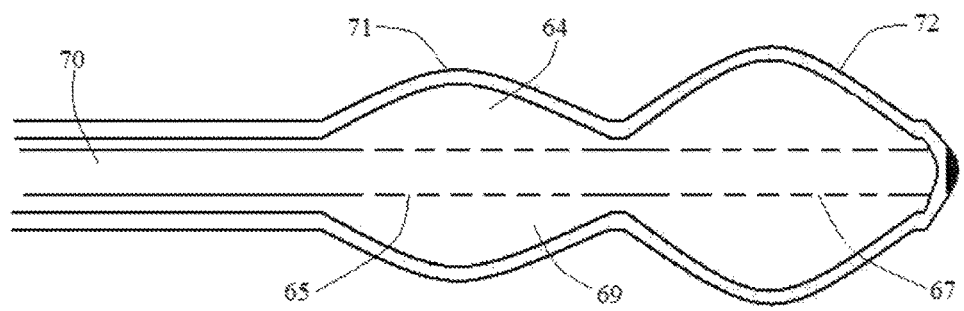
FIG. 28 is a longitudinal cross-sectional view of the device with the balloon in a partially dilated position.
Figure 29:
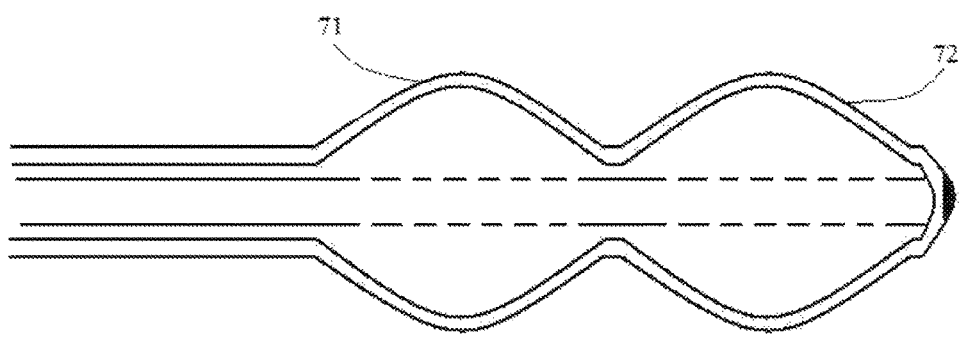
FIG. 29 is a longitudinal cross-sectional view of the device with the balloon in a fully dilated position.

In another embodiment of the device as shown in FIGS. 27-29, the catheter comprises double balloons at the distal heat exchange end. The catheter wall 63 encloses lumens 64 and 69 with a central lumen 70 and a temperature and ICP sensor 68. The central coolant inlet lumen comprises of holes 65 and 67 with a portion in between without holes 66. Pumping of the coolant through the inlet lumen 70 circulates the coolant through holes 65 and 67 with the coolant entering outlet lumens 64 and 69. The balloons 71 and 72 dilate depending on the pressure under which the coolant is pumped. FIG. 28 illustrates the partial dilation of balloon 71 and complete dilation of balloon 72. As more of the coolant is circulated under higher pressure, both the balloons dilate as shown in FIG. 29. This sequential balloon dilation creates a wave in the cerebrospinal fluid surrounding the balloons and facilitates circulation of the cooled cerebrospinal fluid.

Figure 30:
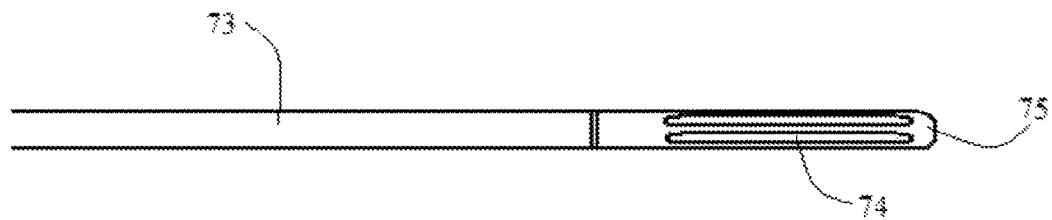
FIG. 30 is a side view of another embodiment the device with the balloon in a contracted position.
Figure 31:
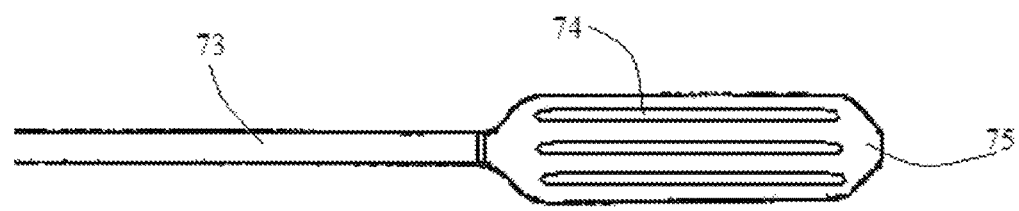
FIG. 31 is a side view of the device with the balloon in a dilated position.

In another embodiment of the device as shown in FIGS. 30 & 31, the catheter distal end comprises of thermal heat conductors 74 in the wall 75. The proximal portion 73 contains and inlet and outlet lumen for coolant circulation and the distal heat conductor portion of the wall 75 can dilate into a balloon as shown in FIG. 31 with the flow of the coolant under pressure. The thermal heat conductors 74 can also comprise of pressure sensors which gauge the extent of balloon dilation by maintaining the central nervous system pressure within a desired range and avoid undue pressure on the surrounding brain.

Figure 32:
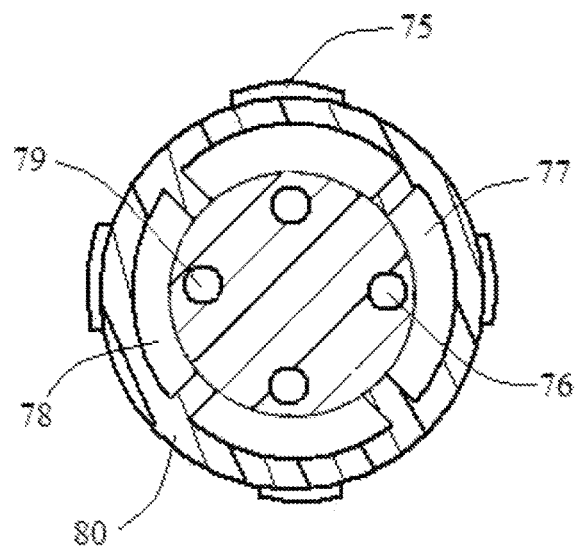
FIG. 32 is a cross-sectional view of another embodiment the device with the balloon in a contracted position.
Figure 33:
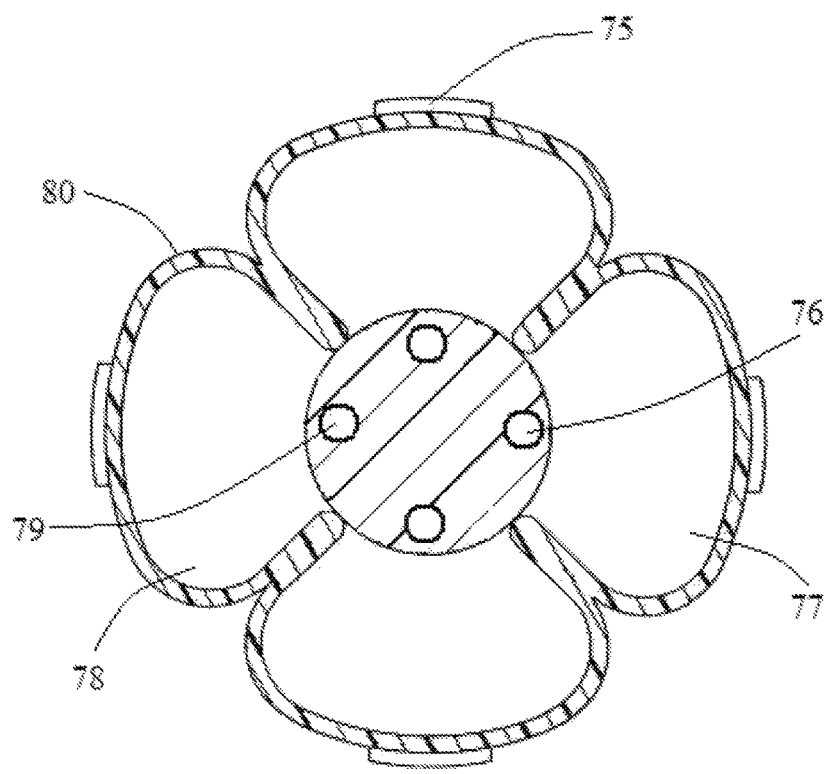
FIG. 33 is a cross-sectional view of the device with the balloon in a dilated position.

In another embodiment of the device as shown in FIGS. 32 and 33, the distal balloon end of the catheter wall 80 comprises of pressure sensors 75. The multiple balloons are arranged in a circumferential format and have an individual inlet 76 and 79 and outlet 77 and 78 ports for coolant circulation. The extent of each balloon 77, 78 dilation is dictated by the pressure on each balloon sensor 75 with the attempt to avoid pressure against the ventricle wall or central nervous system as would normally be undertaken with blind dilation in the prior art. In alternative embodiments, the pressure sensor 75 can also comprise a dual function as a thermal conductor to facilitate heat exchange. FIG. 32 shows the contracted position of the balloons 77 & 78 and FIG. 33 shows the dilated position of the balloons 77 & 78.

Figure 34:
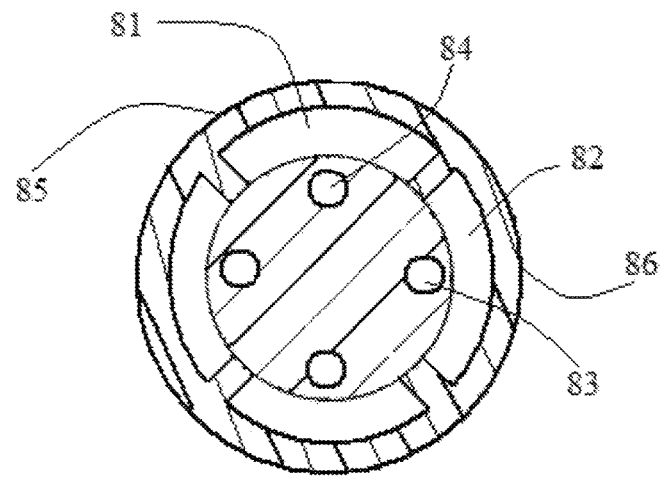
FIG. 34 is a cross-sectional view of another embodiment the device with the balloon in a contracted position.
Figure 35:
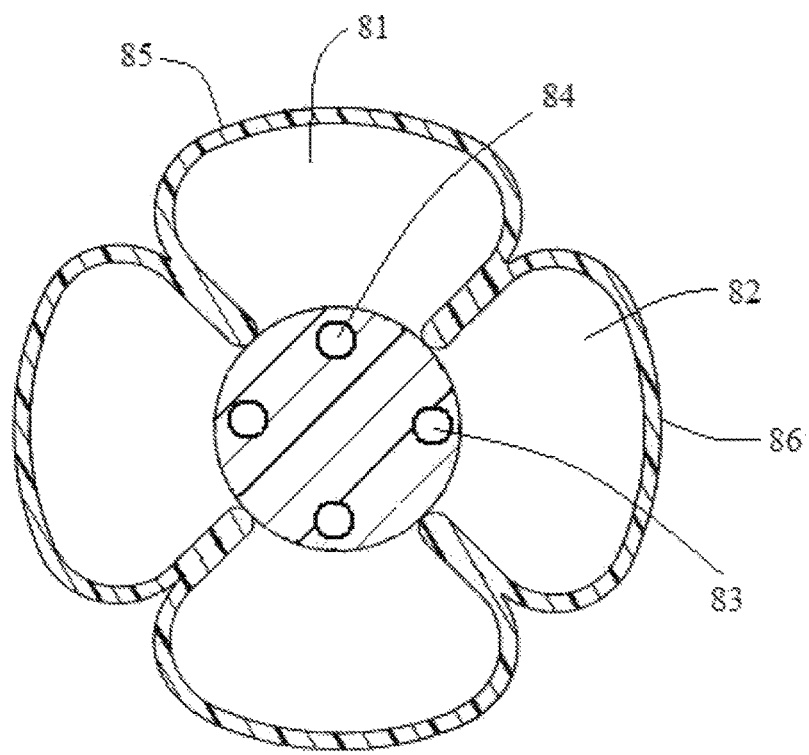
FIG. 35 is a cross-sectional view of the device with the balloon in a dilated position.

In another embodiment of the device as shown in FIGS. 34 and 35, the distal balloon end of the catheter comprises of balloons 85 and 86 each with a coolant inflow lumens 84 and 83 and outflow lumens 81 and 82. The outflow lumens 81 and 82 dilate into balloons once the coolant is circulated as shown in FIG. 35.

Figure 36:
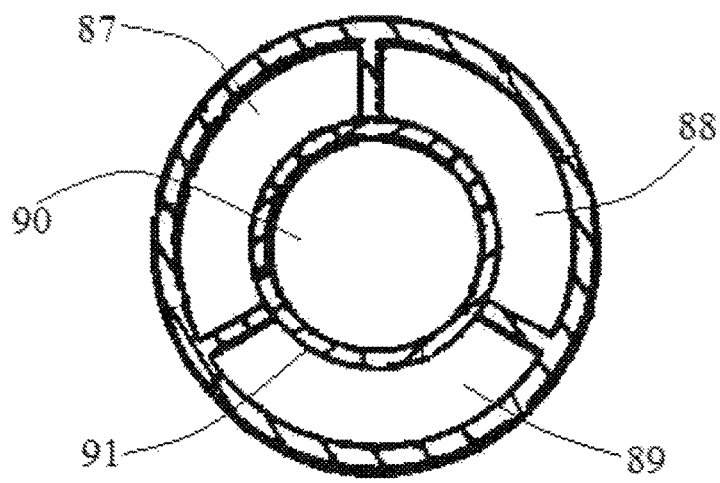
FIG. 36 is a cross-sectional view of another embodiment the device with the balloon in a contracted position.
Figure 37:
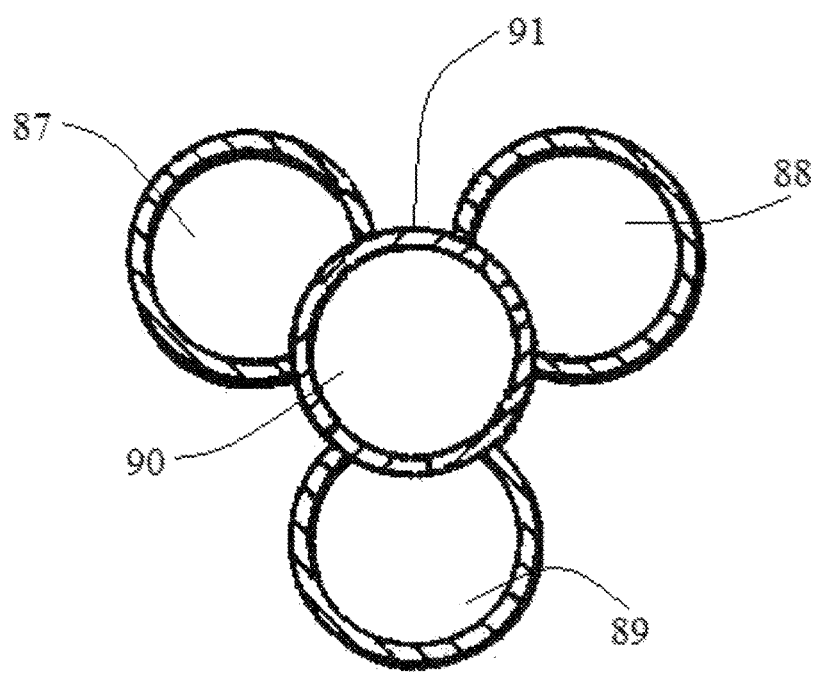
FIG. 37 is a cross-sectional view of the device with the balloon in a dilated position.
Figure 38:
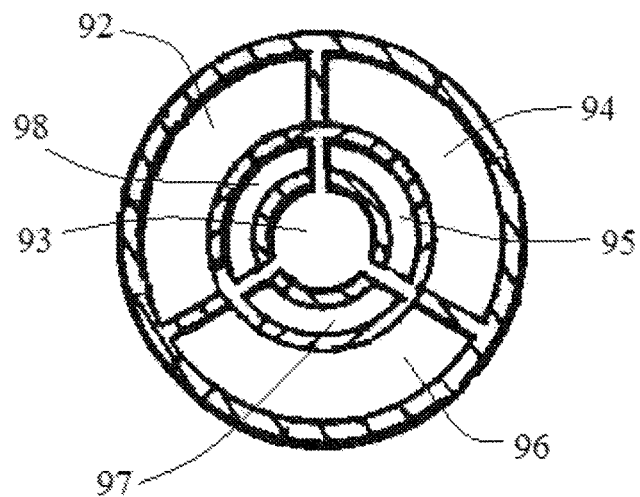
FIG. 38 is a cross-sectional view of another embodiment the device with the balloon in a contracted position.
Figure 39:
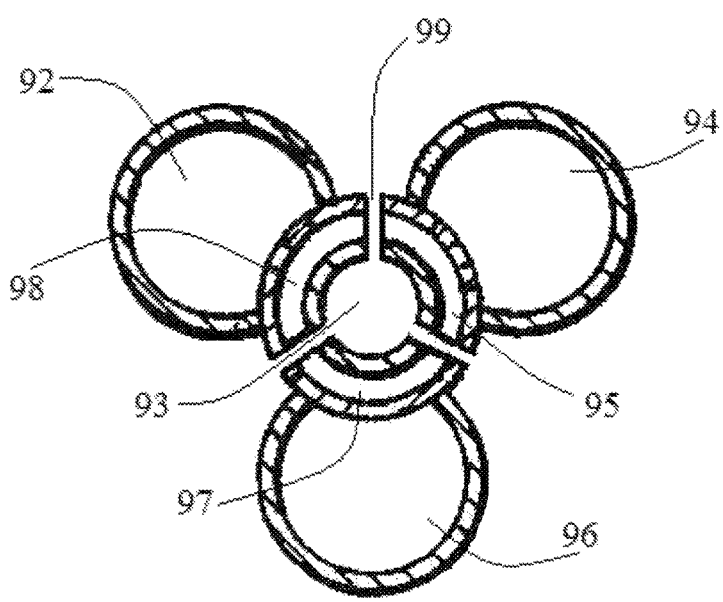
FIG. 39 is a cross-sectional view of the device with the balloon in a dilated position.

In another embodiment of the balloon catheter as shown in FIGS. 36 & 37, the central lumen 90 comprises a wall 91 and circulates a coolant into the multiple balloon lumens 87, 88, and 89 which dilate depending on the pressure of the coolant circulation as shown in FIG. 37. The balloon wall is compliant and adapts to the shape of the path of least resistance in the central nervous system. In alternative embodiments, as shown in FIGS. 38 and 39, the balloons 92, 94, and 96 have individual inflow 98, 95, 97 and outflow coolant lumens. The central lumen 93 communicates with cerebrospinal fluid through ports 99 for drainage and pressure monitoring. FIG. 38 shows the contracted position of the balloons 92, 94, and 96 and FIG. 39 shows the expanded position.

Figure 40:
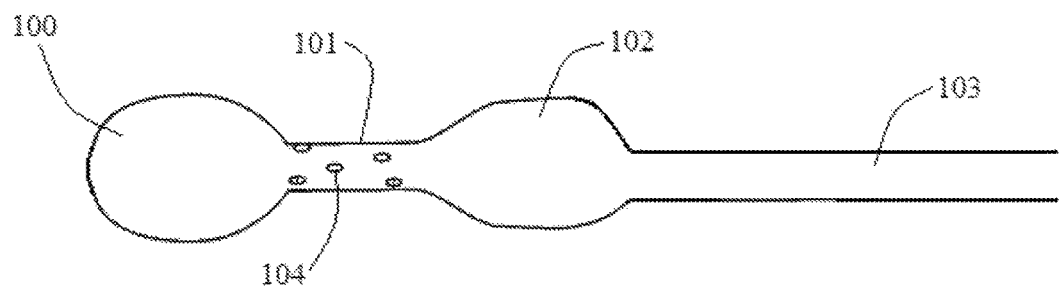
FIG. 40 is a side view of another embodiment the device with the balloon in a dilated position.
Figure 41:
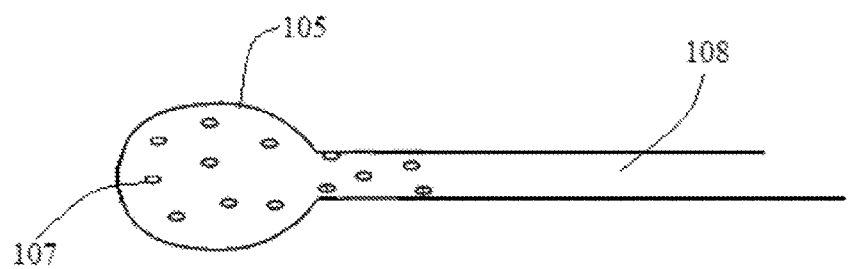
FIG. 41 is a side view of another embodiment the device with the balloon in a dilated position.

FIG. 40 illustrates double balloons 100 and 102 with drainage ports 104 in the catheter wall 101 between the balloons. A coolant is circulated through a closed loop system through the catheter proximal portion 103 connected to a cooler. FIG. 41 illustrates a balloon cooling catheter 108 with drainage ports 107. The drainage ports 107 can also be incorporated into the balloon wall 105.

The methodology and device described provides for treatment of any central nervous system pathology including but not limited to treatment of increased intracranial pressure, brain swelling or edema, spinal cord edema, trauma, brain injury, skull fracture, stroke, ischemia, hypoxia following respiratory or cardiac arrest, tumors, hemorrhage, infection, seizure, spinal cord injury, spine fractures, arteriovenous malformations, aneurysms, aortic artery surgery ischemia protection, spinal stenosis, herniated disc, and scoliosis surgery. The device can be placed intracranial following drilling of a hole in the skull via a twist drill, burr hole placement, or craniotomy/craniectomy. It can be placed inside the spinal canal in the epidural, subdural or subarachnoid space through a percutaneous technique or following a laminotomy/laminectomy. Placement of the device intracranially or intraspinally can be further facilitated by radiographic guidance (fluoroscopy), ventriculograms, cisternograms, ultrasound, frame based or frameless stereotactic navigation systems, or endoscopy. The preferred location of the device is in the cerebrospinal fluid space in the lateral ventricle, subarachnoid space of the brain surface, and lumbar intra-thecal space. Other locations include in the surgical resection bed following craniotomy for removal of brain tumor or hemorrhage and spinal epidural or intrathecal space following a laminectomy. The catheter device can also be secured to the skull by a hollow bolt. The closed loop cooling system selectively cools the central nervous system without serious side-effects of generalized body cooling and in some embodiments also provides for drainage of fluid (cerebrospinal fluid or hemorrhage).

Sensors can be placed in the distal portion of the device positioned inside the central nervous system. These sensors can either be in one location or in multiple locations on the catheter wall. In the preferred embodiment, the sensors monitor pressure and temperature. In other embodiments water sensors can also be positioned to detect cerebrospinal fluid location inside the ventricle to confirm correct catheter location since cerebrospinal fluid predominantly comprises of water. Similarly, impedance sensors can also provide for confirmation of location as the impedance changes from brain to a cerebrospinal fluid location as the catheter is advanced into the lateral ventricle during placement. Other sensors can comprise of cerebrospinal fluid marker sensors, osmolarity sensors, oxygenation sensors, carbonation sensors, metabolite sensors, and pH sensors.

The device with the capability of cooling and circulation of the cerebrospinal fluid provides for selective cooling of the brain and spinal cord. Since the cerebrospinal fluid is in communication from inside the brain to the outer surface of the brain and spinal cord, placement of the device intracranially not only cools the brain but also the spinal cord. Similarly, cooling of the brain can also be achieved by placement of the device inside the spinal canal. Alternatively, one device can be placed intracranially and another in the spinal canal to increase the extent of selective central nervous system cooling.

While the invention and methodology described herein along with the illustrations is specific, it is understood that the invention is not limited to the embodiments disclosed. Numerous modifications, rearrangements, and substitutions can be made with those skilled in the art without departing from the spirit of the invention as set forth and defined herein.

What is claimed is:

1. A method of central nervous treatment comprising the steps of:
    inserting an elongated device into a cerebrospinal fluid, the elongated device including an outside wall, at least one balloon extending from a distal end of the outside wall, the outside wall and the at least one balloon having a lumen formed therein, and an inside wall that extends within the lumen such that a distal end of the inside wall is located within the at least one balloon, the inside wall dividing the lumen into a first lumen part and a second lumen part that communicate at the at least one balloon;
    circulating a coolant through the first and second lumen parts of the lumen; and inflating the at least one balloon with the coolant such that cerebrospinal fluid cooling is facilitated,
    wherein the inside wall is in contact with an inner surface of the outside wall, wherein the inside wall has a drainage lumen formed therein with a plurality of ports located at a distal end of the elongated device that communicate with an outside of the elongated device,
    wherein a distal end of the first lumen part communicates with a distal end of the second lumen part at the at least one balloon, and
    wherein, when the at least one balloon is in a contracted state, the first and second lumen parts of the lumen communicate at the at least one balloon, and
    wherein the plurality of ports of the drainage lumen each extend radially from a central axis of the drainage lumen through the at least one balloon.

2. The method of claim 1, wherein the at least one balloon comprises one of the following shapes: oval, round, cylindrical, triangular, double balloon, helical, angled with respect to the outside wall, a portion or entire lateral ventricle, a frontal horn of a lateral ventricle, a body of a lateral ventricle, a occipital horn of a lateral ventricle, a third ventricle, an operative area in a brain or spine, a cisterna magna, and a spinal canal.

3. The method of claim 1, further comprising pulsating the at least one balloon with the coolant.

4. The method of claim 1, wherein said inserting of the elongated device comprises inserting the elongated device into the cerebrospinal fluid of a brain and/or spinal cord for the central nervous treatment of one or more of the following: hypothermia induction, increased intracranial pressure, trauma, brain injury, skull fracture, stroke, ischemia, hypoxia, tumor, hemorrhage, infection, seizure, swelling/edema, burr hole surgery, craniotomy, decompressive craniectomy, spinal cord injury, spine fracture, ischemia, swelling, infection, tumor, vascular malformation, hemorrhage, stenosis, herniated disc, scoliosis surgery, or aortic aneurysm surgery.

5. The method of claim 1, wherein said insertion of the elongated device into the cerebrospinal fluid comprises performing one or more of the following surgical approaches: craniotomy, burr hole, twist-drill hole, laminectomy, laminotomy, percutaneously, endoscope assisted, stereotactic guidance, and ultrasound guidance.

6. The method of claim 1, wherein said inserting of the elongated device comprises inserting the elongated device into the cerebrospinal fluid of one of the following locations: a lateral ventricle, a cerebral subarachnoid space, a spinal subarachnoid space, a cisterna magna, a third ventricle, and a fourth ventricle.

7. The method of claim 1, wherein the elongated device further includes at least one sensor located at a proximal end of the at least one balloon.

8. The method of claim 1, wherein the inside wall is solid.

9. The method of claim 1, wherein the inside wall includes two planar surfaces that face away from each other.

10. The method of claim 1, wherein at least one of the plurality of ports of the drainage lumen is located at the at least one balloon.

11. The method of claim 1, wherein a central axis of the drainage lumen is coaxial with a central axis of the outside wall.

12. A method for selective central nervous system treatment, the method comprising the steps of:
    inserting an elongated device into a cerebrospinal fluid, the elongated device including an outside wall, at least one surface extending from a distal end of the outside wall, the outside wall and the at least one surface having a lumen formed therein, and the at least one surface being moveable between a dilated position and a contracted position, and an inside wall that extends within the lumen such that a distal end of the inside wall is at a position within the lumen that is defined by the at least one surface, the inside wall dividing the lumen into a first lumen part and a second lumen part that communicate at the at least one moveable surface;
    circulating a coolant through the first and second lumen parts of the lumen; and moving the at least one surface between the contracted position and the dilated position in an alternating manner to facilitate cerebrospinal fluid cooling,
    wherein the inside wall is in contact with an inner surface of the outside wall, wherein the inside wall has a drainage lumen formed therein with a plurality of ports located at a distal end of the elongated device that communicate with an outside of the elongated device,
    wherein a distal end of the first lumen part communicates with a distal end of the second lumen part at the at least one surface, and
    wherein, when the at least one surface is in a contracted state, the first and second lumen parts of the lumen communicate at the at least one surface, and wherein the plurality of ports of the drainage lumen each extend radially from a central axis of the drainage lumen through the at least one surface.

13. The method of claim 12, wherein said moving of the at least one surface comprises expanding and contracting the at least one surface in a pulsating format with said circulating of the coolant by at least one external coolant pump regulator.

14. The method of claim 12, further comprising controlling said circulating of the coolant with at least one regulating mechanism that fluidly communicates with the lumen.

15. The method of claim 12, further comprising creating waves in the cerebrospinal fluid to facilitate circulation of the cooled cerebrospinal fluid throughout the central nervous system.

16. The method of claim 12, wherein the elongated device further includes at least one sensor located at the at least one surface.

17. The method of claim 12, wherein the inside wall is solid.

18. The method of claim 12, wherein the inside wall includes two planar surfaces that face away from each other.

19. The method of claim 12, wherein at least one of the plurality of ports of the drainage lumen is located at the at least one surface.

20. The method of claim 12, wherein a central axis of the drainage lumen is coaxial with a central axis of the outside wall.

* * * * *